(12) United States Patent
Lennox et al.

(10) Patent No.: US 8,597,879 B2
(45) Date of Patent: Dec. 3, 2013

(54) METHODS OF CHARACTERIZING SMALL NUCLEIC ACID MOLECULES

(75) Inventors: Ronald W. Lennox, New York, NY (US); Colin W. Dykes, Gaithersburg, MD (US)

(73) Assignee: Opgen, Inc., Gaithersburg, MD (US)

( * ) Notice: Subject to any disclaimer, the term of this patent is extended or adjusted under 35 U.S.C. 154(b) by 184 days.

(21) Appl. No.: 12/575,703

(22) Filed: Oct. 8, 2009

(65) Prior Publication Data

US 2011/0086344 A1    Apr. 14, 2011

(51) Int. Cl.
   *C12Q 1/68*    (2006.01)

(52) U.S. Cl.
   USPC ........................................................... 435/6.1

(58) Field of Classification Search
   None
   See application file for complete search history.

(56) References Cited

U.S. PATENT DOCUMENTS

| | | | |
|---|---|---|---|
| 5,198,543 A | 3/1993 | Blanco et al. | |
| 5,405,519 A | 4/1995 | Schwartz | |
| 5,599,664 A | 2/1997 | Schwartz | |
| 5,720,928 A * | 2/1998 | Schwartz | 422/186 |
| 6,147,198 A | 11/2000 | Schwartz | |
| 6,150,089 A | 11/2000 | Schwartz | |
| 6,174,671 B1 | 1/2001 | Anantharaman et al. | |
| 6,294,136 B1 | 9/2001 | Schwartz | |
| 6,340,567 B1 | 1/2002 | Schwartz et al. | |
| 6,448,012 B1 | 9/2002 | Schwartz | |
| 6,509,158 B1 | 1/2003 | Schwartz | |
| 6,610,256 B2 | 8/2003 | Schwartz | |
| 6,713,263 B2 | 3/2004 | Schwartz | |
| 2008/0206748 A1 | 8/2008 | Olson et al. | |

FOREIGN PATENT DOCUMENTS

WO    99/53102 A1    10/1999

OTHER PUBLICATIONS

Valouev et al. (Bioinformatics. May 15, 2006;22(10):1217-24. Epub Feb. 24, 2006).*
Nallur et al. (Nucleic Acids Res. Dec. 1, 2001;29(23):E118).*
Zhou et al. (App. Enciron. Microbiol. vol. 68, No. 12 p. 6321-31 at 6323-24 (2002)).*
Cai et al. (Proc. Natl. Acad. Sci. vol. 95, pp. 3390-3395 at 3392 (1998)).*
International Search Report for corresponding case PCT/US2010/043866, mailed Sep. 23, 2010, 4 pp.
Written Opinion for corresponding case PCT/US2010/043866, mailed Sep. 23, 2010, 4 pp.
Valouev et al. Refinement of optical map assemblies. Bioinformatics. May 15, 2006, vol. 22, No. 10, pp. 1217-1224.
Nallur et al. Signal amplification by rolling circle amplification of DNA microarrays. Nucleic Acid Res. Dec. 1, 2001, vol. 29, No. 23, article e118, pp. 1-9.
Jing et al. Automated high resolution optical mapping using arrayed, fluid-fixed DNA molecules. Proc. Natl. Acad. Sci. USA. Jul. 7, 1998, vol. 95, No. 14, pp. 8046-8051.
Xiao et al. Rapid DNA mapping by fluorescent single molecule detection. Nucleic Acids Res. (2007), vol. 35, No. 3, article e16, pp. 1-12.
Khan, "Rolling-Circle Replication of Bacterial Plasmids," *Microb. Molec. Biol. Rev.*, 61(4):442-455 (1997).
Kiefer et al., "Crystal structure of thermostable *Bacillus* DNA polymerase I large fragment at 2.1 Å resolution," *Structure*, 5:95-108 (1997).
Korolev et al., "Crystal structure of the large fragment of *Thermus aquaticus* DNA polymerase I at 2.5-Å resolution: Structural basis for thermostability," *Proc. Natl. Acad. Sci.*, U.S.A., 92:9264-9268 (1995).
Reslewic et al., "Whole-Genome Shotgun Optical Mapping of *Rhodospirillum rubrum*," *Appl. Environ. Microbiol.*, 71(9):5511-5522 (2005).
Samad et al., "Optical Mapping: A Novel, Single-Molecule Approach to Genomic Analysis," *Genome Res.*, 5:1-4 (1995).
Nie, Bei, et al., "Scoring Single-Nucleotide Polymorphisms at the Single-Molecule Level by Counting Individual DNA Cleavage Events on Surfaces," Anal. Chem. 2005, 77, pp. 6594-6600.
Reed, Jason, et al., "Single molecule transcription profiling with AFM*," Nanotechnology 18 (2007) 044032, 15 pages.
Reiss, Edda, et al., "Synthesis and Stretching of Rolling Circle Amplification Products in a Flow-Through System," small (2009), No. 20, pp. 2316-2322.
Supplementary European Search Report for Application No. EP10822381.9 dated Feb. 22, 2013, 7 pages.

* cited by examiner

*Primary Examiner* — Christopher M. Babic
(74) *Attorney, Agent, or Firm* — Thomas C. Meyers; Brown Rudnick LLP

(57)    ABSTRACT

The invention generally relates to methods of characterizing small nucleic acid molecules, such as plasmids or nucleic acid molecules obtained from a virus. In certain embodiments, the invention provides a method of characterizing a small circular nucleic acid molecule, the method including performing rolling circle amplification on a small circular nucleic acid molecule, thereby producing a concatamer, and generating an optical map of the concatamer, thereby characterizing the small circular nucleic acid molecule.

21 Claims, No Drawings

METHODS OF CHARACTERIZING SMALL NUCLEIC ACID MOLECULES

FIELD OF THE INVENTION

The invention generally relates to methods of characterizing small nucleic acid molecules, such as plasmids or nucleic acid molecules obtained from a virus.

BACKGROUND

Physical mapping of genomes, e.g., using restriction endonucleases to develop restriction maps, can provide accurate information about the nucleic acid sequences of various organisms. Restriction maps of, e.g., deoxyribonucleic acid (DNA), can be generated by optical mapping. Optical mapping can produce ordered restriction maps by using fluorescence microscopy to visualize restriction endonuclease cutting events on individual labeled DNA molecules.

Generally, optical maps are produced from digestion of large genomic DNA molecules (e.g., from about 250,000 base pairs to about 2.5 million base pairs). Digestion of large genomic DNA molecules with restriction endonucleases typically used for optical mapping produces restriction fragments ranging from a few base pairs to several hundred thousand base pairs, with an average fragment size typically around 10,000 base pairs. Such large chromosomal DNA fragments typically yield more than 25 internal restriction fragments after digestion.

Identification of DNA molecules by optical mapping generally requires that DNA molecules contain at least 5 internal restriction fragments, usually larger than 1000 base-pairs. Therefore small DNA molecules such as linear plasmids and viruses, and circular plasmids and viruses, that are less than 10,000 base-pairs in size do not normally yield a sufficient number of internal fragments to allow identification based on their internal restriction fragment patterns.

There is an unmet need for methods of characterizing small nucleic acid molecules.

SUMMARY

The invention takes advantage of rolling circle amplification to increase the size of small nucleic acid molecules so that these molecules will behave similarly to large DNA molecules, and thus an optical map of the small nucleic acid molecule can be obtained. Generally, rolling circle amplification is used to generate long, linear concatamers from small single-stranded, or double-stranded, nucleic acid molecules such as plasmids and viruses. The concatamers may reach sizes greater than a hundred thousand base pairs, e.g., more than 20 repeat units of a 4000 base pair monomer. This allows for deposition of the small nucleic acid in the concatamer form, which will behave similarly to large genomic DNA fragments prior to digestion, and thus allow for optical mapping of the small nucleic acid molecule.

An aspect of the invention provides a method of characterizing a small circular nucleic acid molecule (e.g., DNA or RNA) including performing rolling circle amplification on a small circular nucleic acid molecule, thereby producing a concatamer, and generating an optical map of the concatamer, thereby characterizing the small circular nucleic acid molecule. Prior to the performing step, the method can further include circularizing a small linear nucleic acid molecule. Circularizing linear nucleic acid molecules can be accomplished by any technique known in the art, such as using a ligase to generate a circularized nucleic acid molecule from the linear nucleic acid molecule.

Generally, the concatamer will include at least about five internal restriction sites. However, methods of the invention can be carried out with fewer internal restriction sites. The small circular nucleic acid molecule can be a plasmid. The small nucleic acid molecule can be obtained from a virus. The small nucleic acid molecule can be single-stranded or double-stranded.

Another aspect of the invention provides a method of characterizing a small linear nucleic acid molecule including circularizing a small linear nucleic acid molecule to produce a circular nucleic acid molecule, performing rolling circle amplification on the circular nucleic acid molecule, thereby producing a concatamer, and generating an optical map of the concatamer, thereby characterizing the small linear nucleic acid molecule.

Another aspect of the invention provides a method of characterizing a small circular nucleic acid molecule including performing rolling circle amplification on a small circular nucleic acid molecule, thereby producing a concatamer, depositing the concatamer onto a surface such that the concatamer is elongated and fixed on the surface so that the concatamer remains accessible for enzymatic reactions, digesting the concatamer enzymatically to produce one or more restriction digests, imaging the restriction digests, and constructing an optical map from the restriction digests. Prior to the performing step, the method can further include circularizing a small linear nucleic acid molecule. In certain embodiments, the surface is derivatized glass.

DETAILED DESCRIPTION

The invention generally relates to methods of characterizing small nucleic acid molecules (e.g., DNA or RNA), such as plasmids or nucleic acid molecules obtained from a virus. An example of a small nucleic acid molecule is a nucleic acid molecule of 10,000 base pairs or less. Nucleic acid molecules of this size are typically plasmids or nucleic acid molecules from viruses. For example, nucleic acids can be naturally occurring DNA or RNA isolated from any source, recombinant molecules, cDNA, or synthetic analogs, as known in the art. The nucleic acid template may include genomic DNA, DNA fragments (e.g., such as exons, introns, regulatory elements, such as promoters, enhancers, initiation and termination regions, expression regulatory factors, expression controls, and other control regions), DNA including one or more single-nucleotide polymorphisms (SNPs), allelic variants, and mutant nucleic acid.

The nucleic acid template may also be an RNA, such as mRNA, tRNA, rRNA, ribozymes, splice variants, antisense RNA, and RNAi, for example. Also contemplated as useful according to the invention are RNA with a recognition site for binding a polymerase, transcripts of a single cell, organelle or microorganism, and all or portions of RNA complements of one or more cells, for example, cells from different stages of development, differentiation, or disease, and cells from different species. Nucleic acids may be obtained from any nucleic acid source, such as a cell of a person, animal, or plant, or cellular or microbial organism, such as a bacteria, or other infectious agent, such as a virus. Individual nucleic acids may be isolated for analysis, for example, from single cells in a patient sample including cancerous and precancerous cells.

The nucleic acid molecule can be single stranded or double stranded. The nucleic acid molecule can be linear or already circularized. In embodiments in which the small nucleic acid molecule is a linear molecule, the linear nucleic acid molecule can be circularized. Circularizing linear nucleic acid molecules can be accomplished by any technique known in the art, such as using a ligase to generate a circularized nucleic acid molecule from the linear nucleic acid molecule. The ends of a linear template may also be joined by condensing a 5'-phosphate and a 3'-hydroxyl, or a 5'-hydroxyl and a 3'-phosphate. DNA ligase or RNA ligase may be used to enzymatically join the two ends of a linear template, with or without an adapter molecule or linkers, to form a circle. For example, T4 RNA ligase couples single-stranded DNA or RNA, as described in D. C. Tessier et al. (1986) Anal. Biochem., 158: 171-78. CircLigase™ (Epicentre, Madison, Wis.) may also be used to catalyze the ligation of a single stranded nucleic acid. Alternatively, a double stranded E. coli or T4 DNA ligase may be used to join the 5' and 3' ends of a double stranded nucleic acid and the double stranded template denatured prior to annealing to the primer.

In another embodiment, nucleic acid linkers are first ligated to the 5' and 3' ends of a double stranded nucleic acid template, and the linkers are ligated, thereby circularizing the linear double stranded nucleic acid template. The double stranded circular template is then denatured so that a rolling circle amplification primer can be annealed to one of the single template strands. The primer hybridization site preferably spans the ligation site, such that the primer does not hybridize, or hybridized less efficiently, to the linear nucleic acid template.

The circularized small nucleic acid molecule is then subjected to rolling circle amplification. Rolling circle amplification is a method of generating multiple linear copies (concatamers), linked end-to-end, of a circular nucleic acid template. In vivo, bacterial plasmids and some viruses replicate by rolling circle amplification by recruiting host DNA replication proteins, autonomously synthesizing other necessary proteins, and initiating replication by nicking one of the two strands. The replication machinery synthesizes a complementary strand to the remaining circular template, and the self-proteins cleave and circularize the complementary strand replication products into new plasmids. See e.g., Khan (1997) Microb. Molec. Biol. Rev., 61(4): 442-55; and Demidov (Encyclopedia of Diagnostic Genomics and Proteomics, 1175-1179, 2005).

Rolling circle amplification involves effective amounts of reagents including a polymerase, nucleotides, a primer, and a template. Any polymerase capable of performing rolling circle amplification may be used in the reaction, for example, phi 29 DNA polymerase, Taq polymerase, T7 mutant DNA polymerase, T5 DNA polymerase, Klenow, Sequenase, other known DNA polymerases, RNA polymerases, thermostable polymerases, thermodegradable polymerases, and reverse transcriptases. See e.g., Blanco et al., U.S. Pat. Nos. 5,198,543 and 5,001,050; Doublie et al. (1998) Nature, 391: 251-58; Ollis et al. (1985) Nature, 313: 762-66; Beese et al., (1993) Science 260: 352-55; Korolev et al. (1995) Proc. Natl. Acad. Sci. USA, 92: 9264-68; Keifer et al. (1997) Structure, 5:95-108; and Kim et al. (1995) Nature, 376: 612-16. The contents of these patents and articles are incorporated by reference herein in their entirety.

Primers for rolling circle amplification may be synthetically made using conventional nucleic acid synthesis techniques. For example, primers may be synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, and the like. Alternative chemistries, e.g., resulting in non-natural backbone groups, such as phosphorothioate and the like, may also be employed provided that, for example, the resulting oligonucleotides are compatible with the polymerizing agent. The primers may also be ordered commercially from a variety of companies that specialize in custom nucleic acids such as Operon Inc. (Alameda, Calif.).

Rolling circle amplification is used to generate a long, linear concatamer from the small circular nucleic acid molecule. Such concatamers may reach sizes greater than a hundred thousand base-pairs, e.g., more than 20 repeat units of a 4000 base-pair circular monomer. Generally, the concatamer will include at least about five internal restriction sites. However, methods of the invention can be carried out with fewer internal restriction sites. If the monomer contains a single cleavage site for a particular restriction endonuclease, digestion of the concatamer with that restriction endonuclease would yield a series of identical internal restriction fragments, in a repeating pattern characteristic of the monomer. Monomers with two or more restriction sites for a particular restriction endonuclease would give more complex repeat patterns.

Rolling circle amplification allows for deposition of the small nucleic acid molecule to a surface in the concatamer form, which behaves similarly to large genomic DNA fragments prior to digestion, and thus allows one to obtain an optical map of a small nucleic acid molecule. Optical mapping is a single-molecule technique for production of ordered restriction maps from a single DNA molecule (Samad et al., Genome Res. 5: 1-4, 1995).

Various methods can be used for controllable elongation of single nucleic acid molecules in optical mapping and/or sequencing. The methods can be gel-based, solid surface-based, and flow-based (see, e.g., U.S. Pat. No. 6,509,158). During some applications, individual fluorescently labeled DNA molecules are elongated in a flow of agarose between a coverslip and a microscope slide (in a first-generation method) or fixed onto polylysine-treated glass surfaces (in a second-generation method). Samad et al. supra. The added endonuclease cuts the DNA at specific points, and the fragments are imaged. Id. Restriction maps can be constructed based on the number of fragments resulting from the digest. Id. Generally, the final map is an average of fragment sizes derived from similar molecules. Id.

Optical mapping and related methods are described in U.S. Pat. Nos. 5,405,519, 5,599,664, 6,150,089, 6,147,198, 5,720,928, 6,174,671, 6,294,136, 6,340,567, 6,448,012, 6,509,158, 6,610,256, and 6,713,263. All the cited patents are incorporated by reference herein in their entireties.

Optical Maps are constructed as described in Reslewic et al., Appl Environ Microbiol. 2005 September; 71 (9): 5511-22, incorporated by reference herein. Briefly, individual chromosomal fragments from test organisms are immobilized on derivatized glass by virtue of electrostatic interactions between the negatively-charged DNA and the positively-charged surface, digested with one or more restriction endonuclease, stained with an intercalating dye such as YOYO-1 (Invitrogen) and positioned onto an automated fluorescent microscope for image analysis. Since the chromosomal fragments are immobilized, the restriction fragments produced by digestion with the restriction endonuclease remain attached to the glass and can be visualized by fluorescence microscopy, after staining with the intercalating dye. The size of each restriction fragment in a chromosomal DNA molecule is measured using image analysis software and identical restriction fragment patterns in different molecules are used to assemble ordered restriction maps covering the entire chromosome.

Restriction mapping, e.g., optical mapping, can be used in a variety of applications. For example, the methods featured herein can be used to determine a property, e.g., physical and/or chemical property, e.g., size, length, restriction map, weight, mass, sequence, conformational or structural change, pKa change, distribution, viscosity, rates of relaxation of a labeled and/or non-labeled molecule, e.g., an amplicon (e.g., PCR product), of a portion of a genome (e.g., a chromosome), or of an entire genome.

The methods can also be used to identify various organisms, e.g., viruses and prions, and various microorganisms, e.g., bacteria, protists, and fungi, whose genetic information is stored as DNA or RNA by correlating the restriction map of a nucleic acid of an organism with a restriction map database. Such identification methods can be used in diagnosing a disease or disorder. Methods of identifying organisms by restriction mapping are described, e.g., in a U.S. patent application Ser. No. 12/120,586, filed on May 14, 2008, incorporated herein by reference.

The methods featured herein can also be used in other diagnostic applications, for example, imaging specific loci or genetic regions for individuals or populations to help identify specific diseases or disorders. Other uses of the methods will be apparent to those skilled in the art.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method of characterizing a nucleic acid molecule, the method comprising:
   performing rolling circle amplification on a nucleic acid molecule of 1,000 base pairs or fewer, thereby producing a concatamer; and
   generating an optical map of the concatamer, thereby characterizing the nucleic acid molecule.

2. The method according to claim 1, wherein prior to said performing step, the method further comprises circularizing a nucleic acid molecule of 1,000 base pairs or fewer.

3. The method according to claim 1, wherein the concatamer comprises at least five internal restriction sites.

4. The method according to claim 1, wherein the nucleic acid molecule is DNA or RNA.

5. The method according to claim 1, wherein the nucleic acid molecule is a plasmid.

6. The method according to claim 1, wherein the nucleic acid molecule is obtained from a virus.

7. The method according to claim 1, wherein the nucleic acid molecule is single-stranded.

8. The method according to claim 1, wherein the nucleic acid molecule is double-stranded.

9. A method of characterizing a nucleic acid molecule, the method comprising:
   circularizing a nucleic acid molecule of 1,000 base pairs or fewer to produce a circular nucleic acid molecule;
   performing rolling circle amplification on the circular nucleic acid molecule, thereby producing a concatamer; and
   generating an optical map of the concatamer, thereby characterizing the nucleic acid molecule.

10. The method according to claim 9, wherein the concatamer comprises at least five internal restriction sites.

11. The method according to claim 9, wherein the nucleic acid molecule is DNA or RNA.

12. The method according to claim 9, wherein the nucleic acid molecule is obtained from a virus.

13. The method according to claim 9, wherein the nucleic acid molecule is single-stranded.

14. The method according to claim 9, wherein the nucleic acid molecule is double-stranded.

15. A method of characterizing a nucleic acid molecule, the method comprising:
   performing rolling circle amplification on a nucleic acid molecule of 1,000 base pairs or fewer, thereby producing a concatamer;
   depositing the concatamer onto a surface such that the concatamer is elongated and fixed on the surface so that the concatamer remains accessible for enzymatic reactions;
   digesting the concatamer enzymatically to produce one or more restriction digests;
   imaging the restriction digests; and
   constructing an optical map from the restriction digests.

16. The method according to claim 15, wherein prior to said performing step, the method further comprises circularizing a nucleic acid molecule of 1,000 base pairs or fewer.

17. The method according to claim 15, wherein the concatamer comprises at least five internal restriction sites.

18. The method according to claim 15, wherein the nucleic acid molecule is DNA or RNA.

19. The method according to claim 15, wherein the surface is derivatized glass.

20. The method according to claim 15, wherein the nucleic acid molecule is a plasmid.

21. The method according to claim 15, wherein the nucleic acid molecule is obtained from a virus.

* * * * *